(12) United States Patent
Batzinger et al.

(10) Patent No.: US 6,792,808 B1
(45) Date of Patent: Sep. 21, 2004

(54) ULTRASONIC INSPECTION METHOD

(75) Inventors: Thomas James Batzinger, Burnt Hills, NY (US); Li Wei, Mill Creek, WA (US); John Broddus Deaton, Jr., Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 10/426,444

(22) Filed: Apr. 30, 2003

(51) Int. Cl.$^7$ .......................... G01P 29/00; G01P 29/04
(52) U.S. Cl. .......................... 73/602; 73/624; 73/625; 73/628
(58) Field of Search .................. 73/596–600, 601–602, 73/624–628, 632, 641

(56) References Cited

U.S. PATENT DOCUMENTS

| | | | |
|---|---|---|---|
| 3,052,115 A | * | 9/1962 | Renaut et al. ............. 73/626 |
| 4,180,790 A | | 12/1979 | Thomas |
| 4,180,791 A | | 12/1979 | Tiemann |
| 4,604,897 A | * | 8/1986 | Saglio .................... 73/626 |
| 5,014,712 A | | 5/1991 | O'Donnell |
| 5,065,629 A | * | 11/1991 | Koike et al. ............. 73/602 |
| 5,111,695 A | | 5/1992 | Engeler et al. |
| 5,230,340 A | | 7/1993 | Rhyne |
| 5,235,982 A | | 8/1993 | O'Donnell |
| 5,329,930 A | | 7/1994 | Thomas, III et al. |
| 5,345,939 A | | 9/1994 | Engeler et al. |
| 5,487,306 A | | 1/1996 | Fortes |
| 5,568,813 A | | 10/1996 | Deitrich et al. |
| 5,817,023 A | | 10/1998 | William Daft |
| 5,853,367 A | | 12/1998 | Chalek et al. |
| 5,891,038 A | | 4/1999 | Seyed-Bolorforosh et al. |
| 5,897,501 A | | 4/1999 | Wildes et al. |
| 5,902,241 A | | 5/1999 | Seyed-Bolorforosh et al. |
| 5,951,479 A | | 9/1999 | Holm et al. |
| 6,048,315 A | | 4/2000 | Chiao et al. |
| 6,056,693 A | | 5/2000 | Haider |
| 6,183,419 B1 | | 2/2001 | Wildes |
| 6,210,332 B1 | | 4/2001 | Chiao et al. |
| 6,253,618 B1 | * | 7/2001 | Wooh .................... 73/602 |
| 6,279,399 B1 | * | 8/2001 | Holm .................... 73/626 |
| 6,296,612 B1 | | 10/2001 | Mo et al. |

OTHER PUBLICATIONS

U.S. application Ser. No. 10/244,637, "Phased Array Ultrasonic Inspection Method for Industrial Applications", filed Sep. 16, 2002, Docket No. 128500.

* cited by examiner

*Primary Examiner*—Helen Kwok
(74) *Attorney, Agent, or Firm*—Penny A. Clarke; Patrick K. Patnode

(57) ABSTRACT

An ultrasonic inspection method includes exciting a first set of transducers in an array to introduce ultrasonic energy into a component, generating a number of echo signals using a second set of transducers in the array as receive elements, and processing the echo signals. The first and second sets of transducers are exclusive of one another, and the first and second sets of transducers are interleaved.

11 Claims, 10 Drawing Sheets

ULTRASONIC INSPECTION METHOD

BACKGROUND OF THE INVENTION

The invention relates generally to ultrasonic imaging methods and, more particularly, to improved near surface resolution for phased array ultrasonic inspection of industrial components.

Phased array imaging ultrasound systems are a promising tool for industrial inspections. However, conventional ultrasonic inspection methods exhibit poor near surface resolution for certain inspection configurations. In particular, it is often desirable to perform an ultrasonic inspection where a transducer is located in close proximity to the test object (such as a component or structure, collectively termed "component" herein), in order to focus the ultrasound within the test object. However, industrial components, such as forgings, produce a strong reflection of the ultrasound from the surface of the component. The corresponding "interface signal" has a relatively long duration, reducing the ability to detect defects near the surface of the component. FIG. 1 illustrates the conventional transmit/receive pattern for inspection of a component using phased array ultrasound. The corresponding predicted interface signal is shown in FIG. 2. Because of the relatively long interface signal, the signals that correspond to defects near the surface of the component are difficult to identify and characterize, decreasing the near surface resolution of the phased array ultrasonic inspection.

This near surface resolution issue for ultrasonic inspections has been addressed in different ways. One solution is to perform conventional ultrasonic inspection using a fixed geometry transducer instead of a phased array system. By "fixed geometry," it is meant that the transducer has fixed focal properties. The transducer is scanned over the surface of the component several times along a predefined path (raster, circumferential, etc.), with each scan being performed at a different distance from the surface of the component. By adjusting the separation between the transducer and the component surface, each successive scan moves the focus of the scan further into the component. The interrogation gates used to monitor the signal from the component are moved accordingly to inspect the component at various depths. Although this method permits near surface resolution of defects, it is time consuming because it involves repeated inspections of the component.

Another solution is to inspect the industrial component, for example a forging, using the conventional phased array inspection technique described above with reference to FIG. 1. To compensate for the poor near surface resolution, the forging is made slightly larger than the desired final size. After the inspection, the forging is machined down to the desired size. Removal of the outer portion of the material renders the poor near surface resolution less important. However, this method is expensive as it involves using excess material for the forgings and extra machining steps.

Accordingly, it would be desirable to develop an ultrasonic inspection method for industrial applications, such as the inspection of aircraft engine forgings, that provides improved near surface resolution, without requiring the use of repeated scans at various distances from the surface of the test object.

SUMMARY OF THE INVENTION

Briefly, in accordance with one embodiment of the present invention, an ultrasonic inspection method includes exciting a first set of transducers in an array to introduce ultrasonic energy into a component, generating a number of echo signals using a second set of transducers in the array as receive elements, and processing the echo signals. The first and second sets of transducers are exclusive of one another, and the first and second sets of transducers are interleaved.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 3:
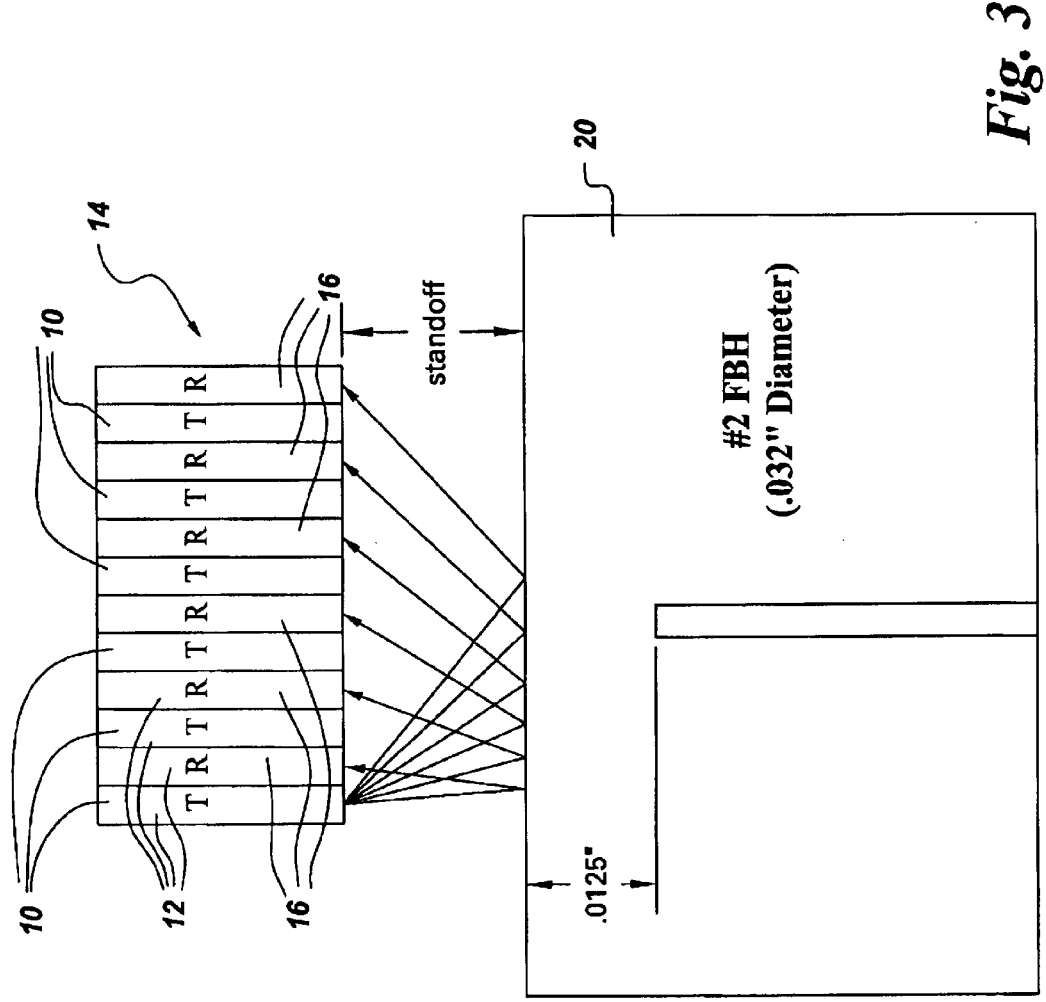
FIG. 3 illustrates the ultrasonic inspection method of the present invention.
Figure 4:
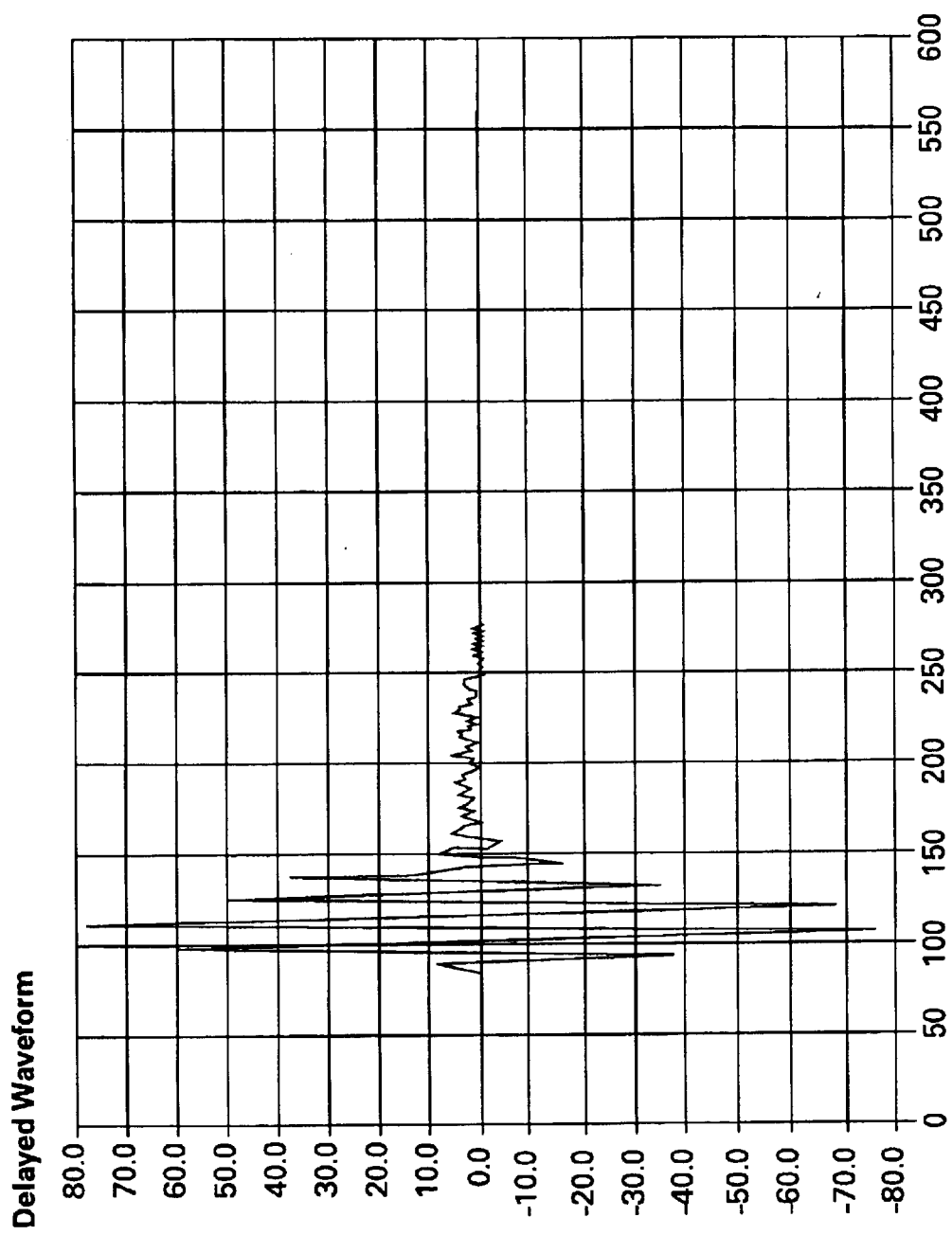
FIG. 4 shows a predicted interface signal for the ultrasonic inspection method illustrated by FIG. 3.
Figure 6:
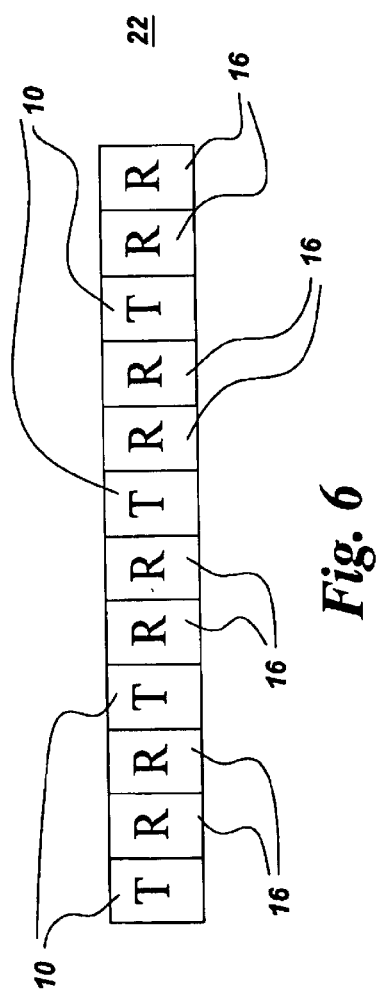
FIG. 6 depicts an exemplary interleaved pattern of transducers configured as transmit and receive elements.
Figure 7:
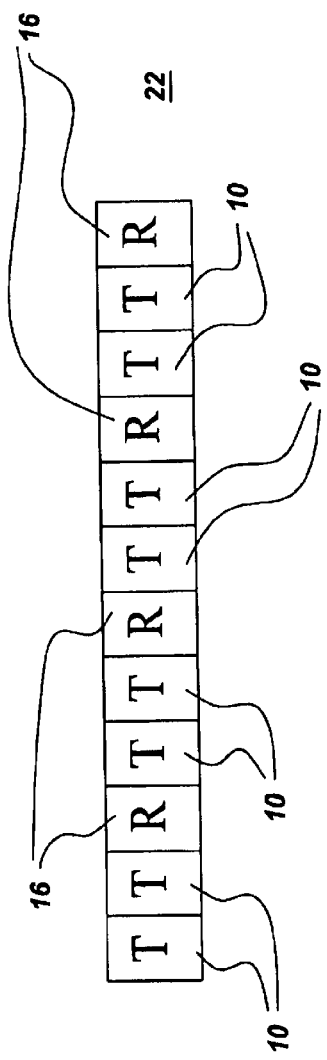
FIG. 7 depicts another exemplary interleaved pattern of transducers configured as transmit and receive elements.
Figures 8, 9:
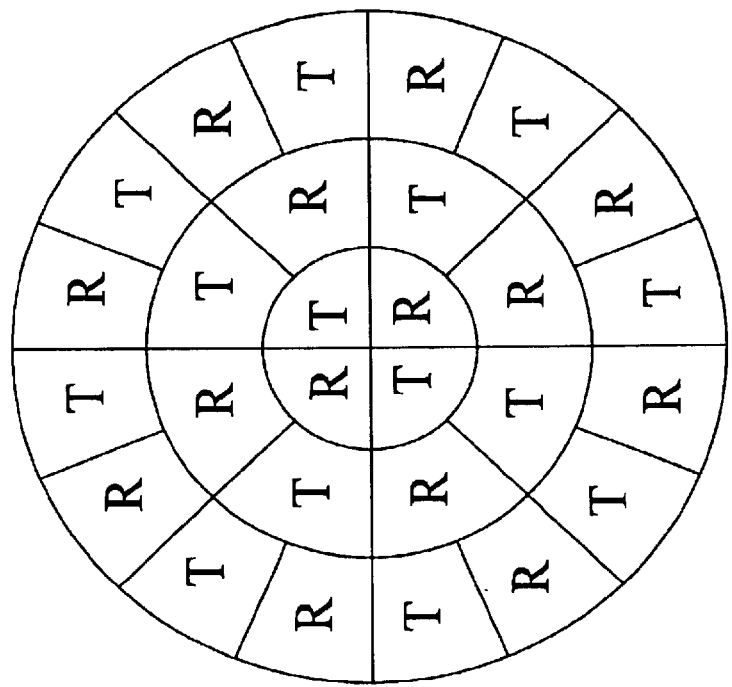
FIG. 8 shows an exemplary two dimensional phased array.
FIG. 9 shows an exemplary sectorial phased array.

An ultrasonic inspection method of the invention is described with reference to FIG. 3. As shown, the method includes exciting a first set 10 of transducers 12 in an array 14 to introduce ultrasonic energy into a component 20. The transducers 12 in the first set 10 are indicated by the letter "T" in FIG. 3 and are referred to as transmit elements T herein. The method further includes generating a number of echo signals using a second set 16 of transducers in the array as receive elements and processing the echo signals. The receive elements are indicated by the letter "R" in FIG. 3. As indicated in FIG. 3, the first and second sets of transducers 10, 16 are (1) exclusive of one another and (2) interleaved. By the phrase "exclusive of one another," it is meant that a transducer 12 is either a member of the first set 10 or a member of the second set 16, such that a transducer 12 is not a member of both the first and second sets 10, 16. In other words, each of the transducers 12 forming the array 14 is controlled either to transmit or receive. By the term "interleaved," it is meant that at least one transmit element T is situated between receive elements R, and at least one receive element R is situated between transmit elements T. Exemplary interleaved first and second sets 10, 16 of transducers include the alternating pattern shown in FIG. 3, as well as the patterns shown in FIGS. 6 and 7.

Figure 5:
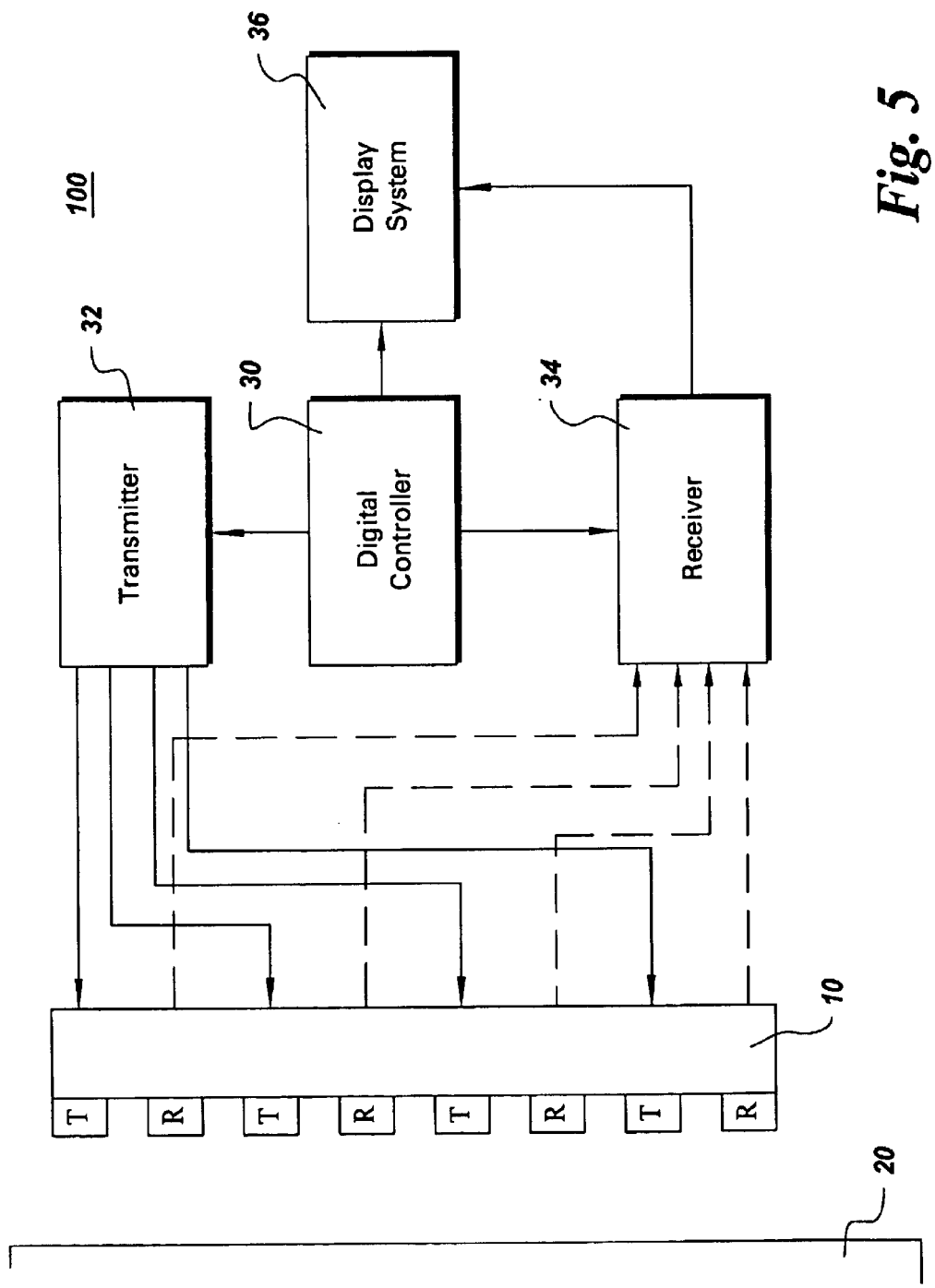
FIG. 5 is a block diagram of an exemplary ultrasonic imaging system for performing the ultrasonic inspection method of FIG. 3.

An exemplary ultrasonic imaging system 100 is illustrated in FIG. 5. As shown, each of the transducers 12 in the first set 10 is excited, for example, by a pulse produced by a transmitter 32. The resulting ultrasonic energy penetrates the component 20 and is reflected back to the array 14. To generate the echo signals, the ultrasonic energy reflected back to the array 14 is converted to an electrical signal (echo signal) by each of the transducers 12 in the second set 16 and applied separately to a receiver 34. For the exemplary system shown in FIG. 5, the transmitter 32 and receiver 34 are controlled by a digital controller 30 responsive to commands input by an operator. The echo signals may be processed using know imaging software, under the control of digital controller 30, and displayed on display system 36.

Figure 1:
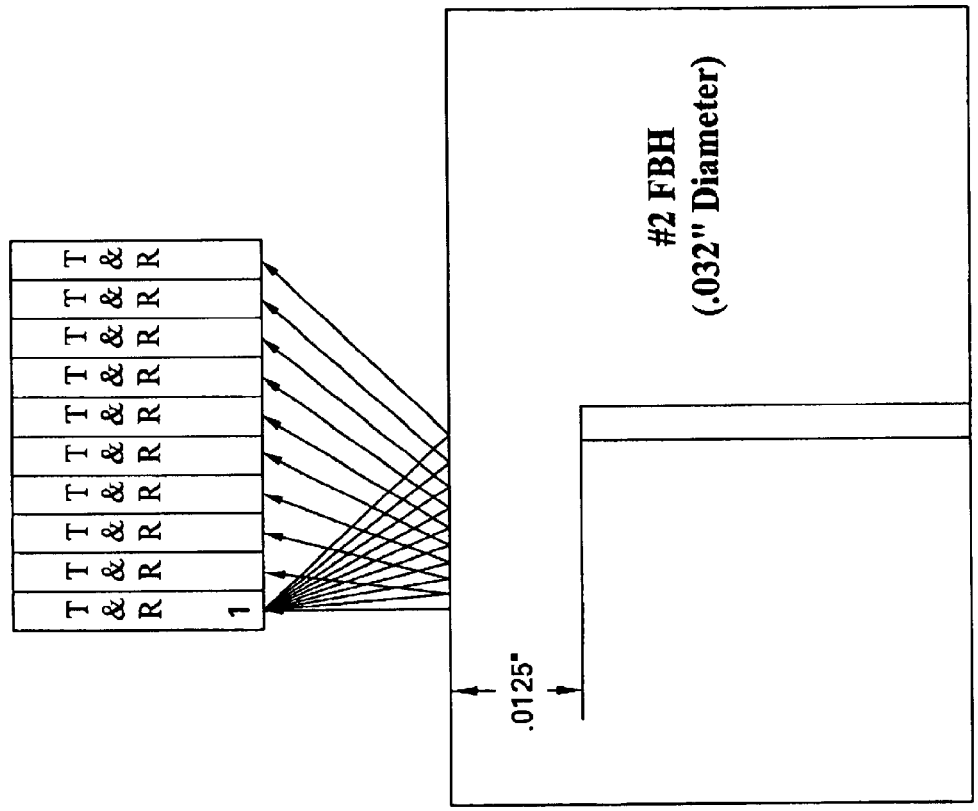
FIG. 1 shows a conventional transmit and receive pattern for a phased array ultrasonic inspection of a component.
Figure 2:
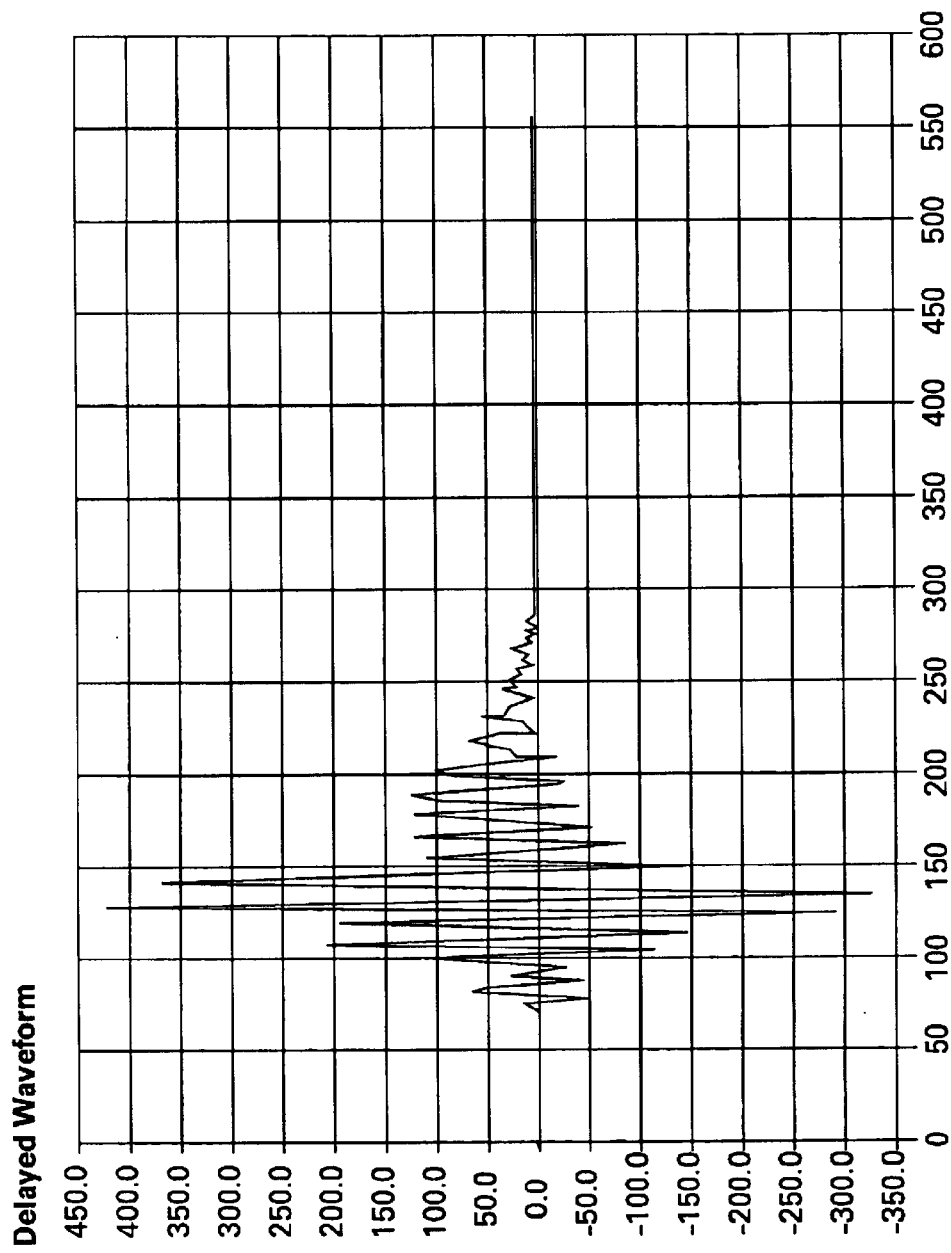
FIG. 2 shows a predicted interface signal for the conventional transmit and receive pattern of FIG. 1.
Figure 11:
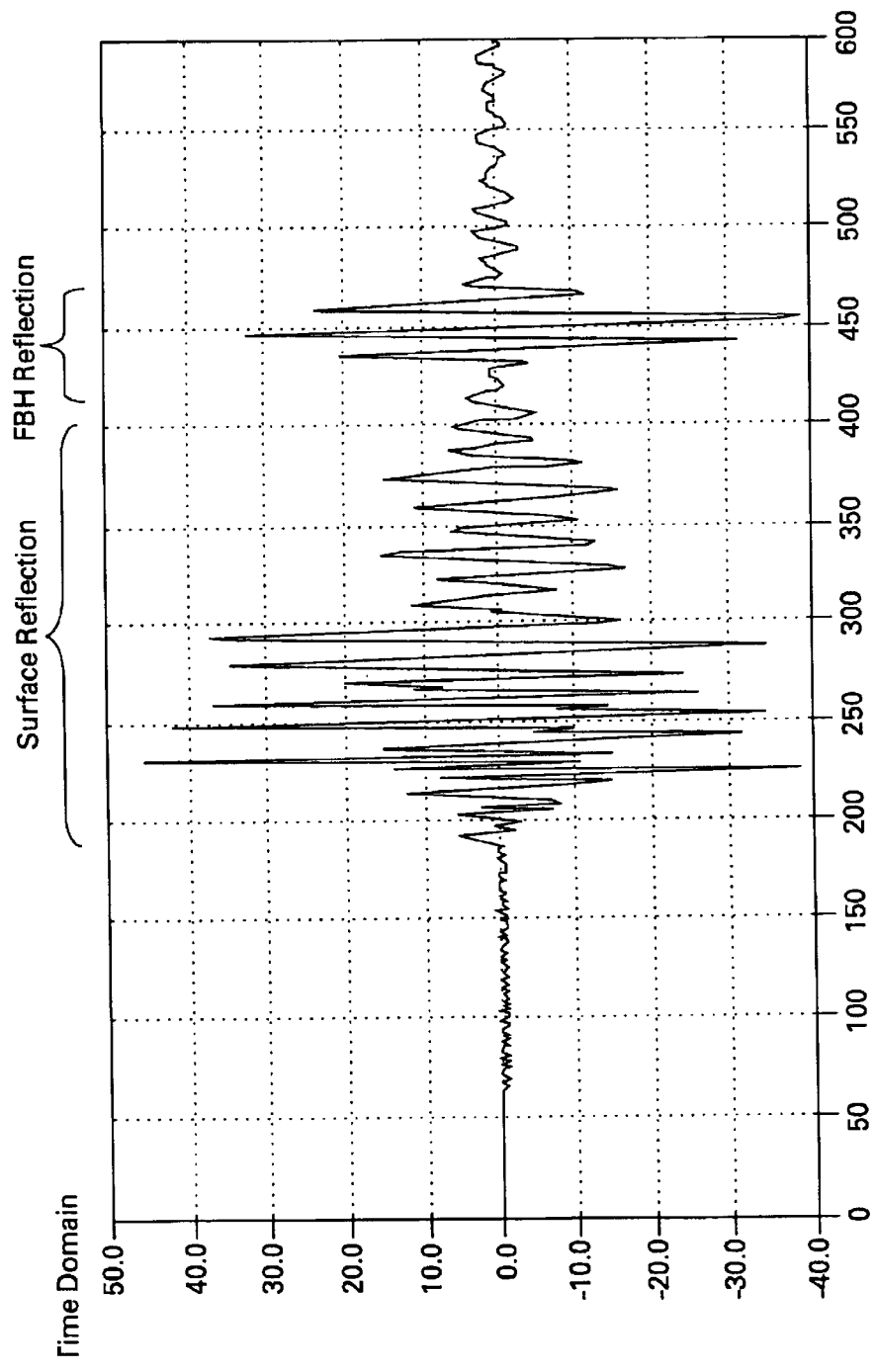
FIG. 11 shows an echo signal for the conventional transmit and receive pattern of FIG. 1.
Figure 12:
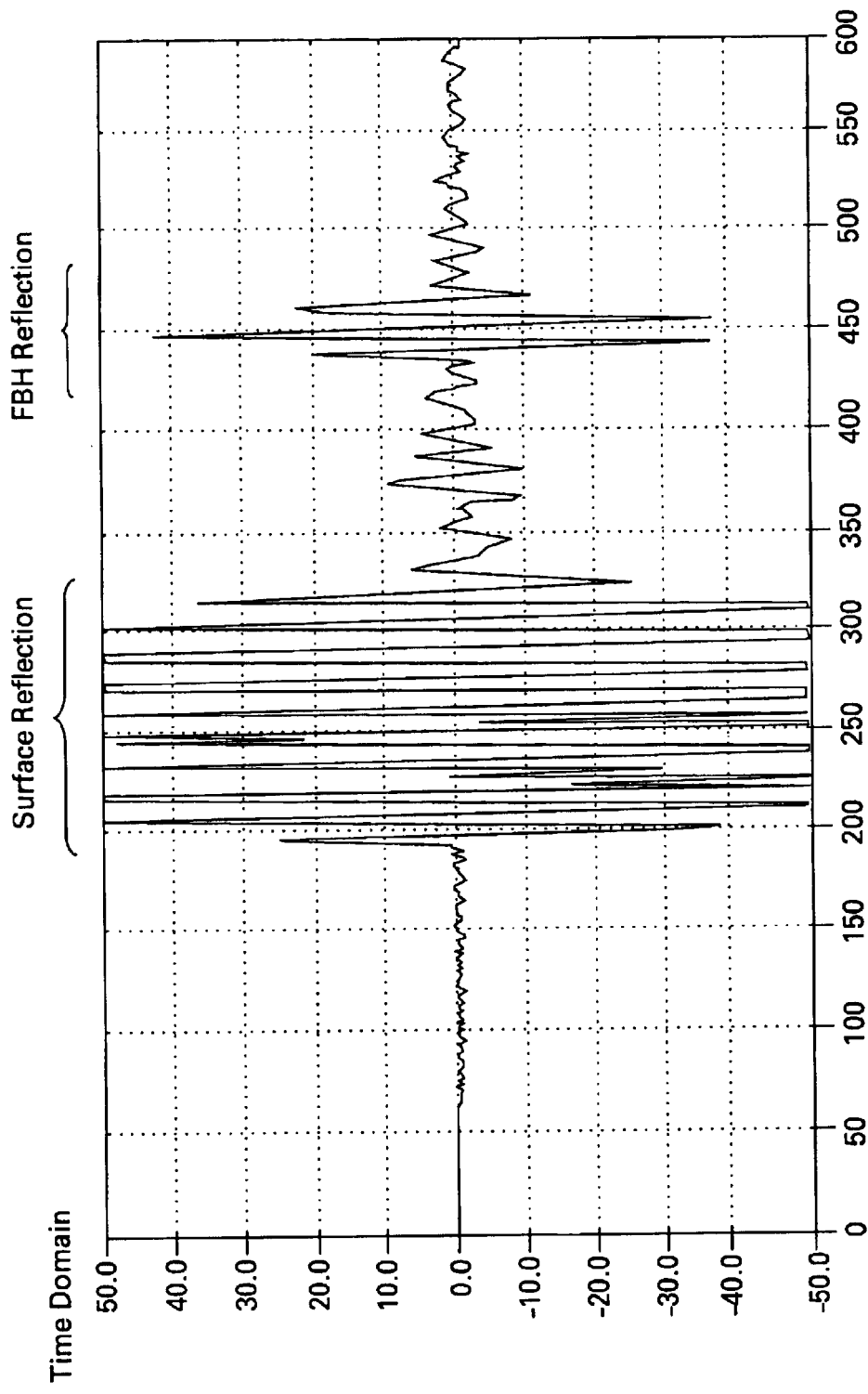
FIG. 12 shows an echo signal for the ultrasonic inspection method of FIG. 3.

As noted above, for ultrasonic imaging, it is desirable to reduce the interface signal, namely to reduce the signal that corresponds to reflection of the ultrasound off the surface 28 of the component 20. Beneficially, transmitting and receiving with separate sets of interleaved transducers eliminates the contribution to the interface signal of the ultrasound that is transmitted by a transducer T/R, reflected from the surface and received by the same transducer T/R that is present using the conventional transmit/receive pattern of FIG. 1. Because this sound path from a transducer T/R to the surface 28 and back to the same transducer T/R is the shortest sound path for the conventional transmit/receive pattern of FIG. 1, it undesirably contributes to the length of the interface signal. By eliminating such contributions to the interface signal, the interface signal is reduced, which in turn improves the resolution near the surface 28 of the component 20. The improved near surface resolution of the inventive ultrasonic inspection method is illustrated by a comparison of FIGS. 11 and 12. FIG. 11 shows an echo signal obtained using a conventional transmit and receive pattern. As shown, the interface signal has a long duration. In contrast, the interface signal is shorter and the defect signal easier to resolve, for the echo signal shown in FIG. 12, which was obtained using the ultrasonic inspection method of the present invention.

For the arrangement of FIG. 3, the array 14 and the component 20 are separated by a standoff. The thickness of the standoff depends on the design of the array 14. For industrial applications, exemplary standoffs include water, other fluids such as oils and glycerine, a machined wedge (shoe), and combinations thereof. Examples of shoes (not shown) are solid structures machined to mate with the geometry of the transducer surface, on one side, and the component geometry on the other side. Shoes are often formed of plexiglass or Lucite. Industrial components 20, such as aircraft engine disk forgings 20, have significantly different material velocities than the standoffs. This material velocity mismatch enhances the reflection of the ultrasound from the surface 28. Accordingly, the inventive method described above is particularly desirable for the ultrasonic inspection of industrial components 20, such as forgings 20.

The ultrasonic inspection method described above can be performed using various array 14 sizes and types. For example, small arrays 14 having 32 transducers 12 may be used. To provide a large inspection area, the array 14 may contain a large number of transducers 12, for example 128 or 1024. The ultrasonic inspection method described above can be employed for linear phased arrays 22, as shown for example in FIGS. 6 and 7. The ultrasonic inspection method may also be used for a two-dimensional phased array 24, as shown for example in FIG. 8, and for a sectorial phased array 26, as exemplarily indicated in FIG. 9. The interleaved patterns of transducers 12 configured as transmit and receive elements T, R in FIGS. 6–9 are exemplary.

Figure 10:
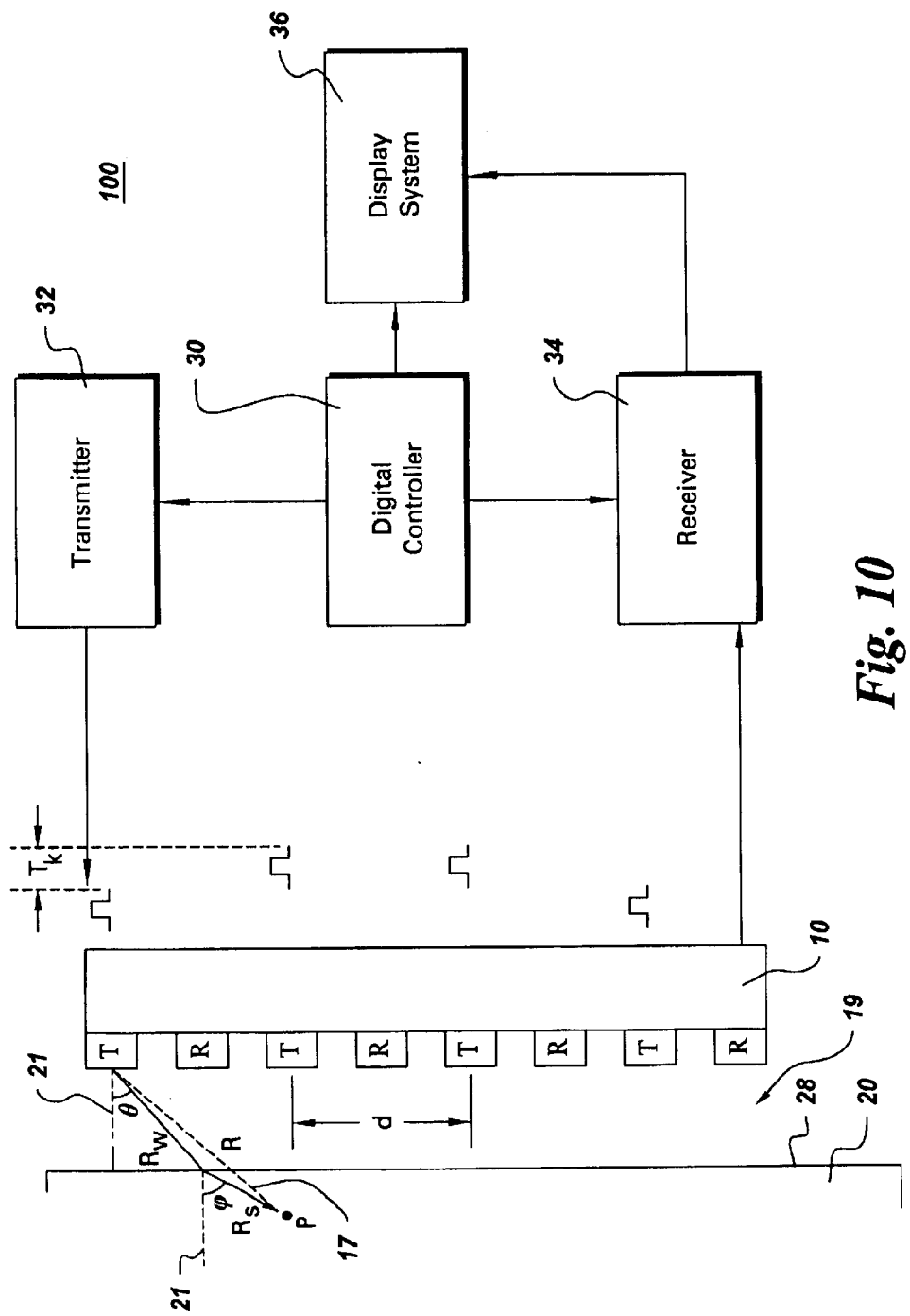
FIG. 10 illustrates the ultrasonic inspection method with beam focusing.

To focus the ultrasonic energy at a focal point P in the component, a delay profile $\{T_k\}$ is employed for a more particular embodiment of the inventive method, which is described with reference to FIG. 10. The transmit delay profile comprises a set of transmit delays. Exemplary transmit delays include time and/or phase delays, which are also indicated in FIG. 10 by $T_k$. As indicated in FIG. 10, a number of excitation signal pulses are modulated with a transmit delay profile $\{T_k\}$ to generate a number of modulated excitation signal pulses. A separate one of the modulated excitation signal pulses is applied to each of the transducers 12 in the first set 10, to excite the first set 10 of transducers 12. For example, transmitter 32 imparts a transmit delay to each of the signal pulses applied to the successive transducer elements 12 in the first set 10. If the transmit delay is zero ($T_k$=0), all of the transducer elements 12 in the first set 10 are energized simultaneously, and the resulting ultrasonic beam is directed normal to the surface 28 of the component 10. To focus the ultrasonic energy at a focal point P in the component, the transmit delay $T_k$ that is added to the respective kth signal pulse from one end of the array 14 (k=1) to the other end (k=N) can be expressed as:

$$T_k = (k-(N-1)/2)^2 d^2 \cos^2\theta / 2Rv,$$

where N is the number of transmit elements (transducers 12) in the first set 10, and d is the distance between transducer elements 12 in the first set 10, as shown in FIG. 10. In addition, R is the range of the focal point P from the center of the first set 10 of transducers 12, v is the material velocity of the component 20, and $\theta$ is the angle of incidence for the beam 17 relative to a surface normal 21.

As explained in commonly assigned, pending U.S. patent application Ser. No. 10/244,637, Batzinger et al., entitled "Phased Array Ultrasonic Inspection Method for Industrial Applications," which is hereby incorporated by reference, it is desirable for the transmit delay profile $\{T_k\}$ to compensate for the refraction of the ultrasonic beam at the surface 28 of the component 20. The following expression for the transmit delay $T_k$ compensates for the refraction of the ultrasonic beam at the surface 28:

$$T_k = [k-(N-1)/2]^2 d^2 \cos^2\theta / [2(R_w v_w + R_s v_s)],$$

where $R_w$ is the length of the beam extending along the central beam axis 17 in the standoff 19, $v_w$ is the material velocity in the standoff 19, $R_s$ is the length of the beam extending along the central beam axis 17 in the component 20, and $v_s$ is the material velocity in the component shown in FIG. 10.

Although only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. An ultrasonic inspection method comprising:
    exciting a first set of transducers in a phased array to introduce ultrasonic energy into a component;
    generating a plurality of echo signals using a second set of transducers in the phased array as receive elements; and
    processing the echo signals,
    wherein the first and second sets of transducers are exclusive of one another, and wherein the first and second sets of transducers are interleaved; and wherein the phased array reduces a time duration of an interface signal.

2. The ultrasonic inspection method of claim 1, wherein the array and the component are separated by a standoff.

3. The ultrasonic inspection method of claim 1, wherein the array comprises a linear phased array.

4. The ultrasonic inspection method of claim 1, wherein the array comprises a two-dimensional phased array.

5. The ultrasonic inspection method of claim 1, wherein the array comprises a sectorial phased array.

6. The ultrasonic inspection method of claim 1, wherein said exciting of the first set of transducers comprises modulating a plurality of excitation signal pulses with a transmit delay profile to generate a plurality of modulated excitation signal pulses, and applying a separate one of the modulated excitation signal pulses to each of the transducers in the first set.

7. A near surface resolution method for inspecting a forging, said method comprising:

exciting a first set of transducers in a phased array to introduce ultrasonic energy into a forging;

generating a plurality of echo signals using a second set of transducers in the phased array as receive elements; and processing the echo signals, wherein the first and second sets of transducers are exclusive of one another, and wherein the first and second sets of transducers are interleaved; and wherein the phased array reduces a time duration of an interface signal.

8. The near surface resolution method of claim 7, wherein the array and the forging are separated by a standoff.

9. The near surface resolution inspection method of claim 7, wherein the array comprises a linear phased array.

10. The near surface resolution inspection method of claim 7, wherein said exciting of the first set of transducers comprises modulating a plurality of excitation signal pulses with a transmit delay profile to generate a plurality of modulated excitation signal pulses, and applying a separate one of the modulated excitation signal pulses to each of the transducers in the first set.

11. The near surface resolution inspection method of claim 7, wherein the forging comprises an aircraft disk forging.

* * * * *